(12) United States Patent
Grim et al.

(10) Patent No.: US 10,722,648 B2
(45) Date of Patent: *Jul. 28, 2020

(54) FLUID MANAGEMENT SYSTEMS FOR SURGICAL PROCEDURES

(71) Applicant: Covidien LP, Mansfield, MA (US)

(72) Inventors: Kasey A. Grim, Boulder, CO (US); Joe D. Sartor, Longmont, CO (US); Valery E. Meusburger, Highlands Ranch, CO (US); Rachel C. Grosskrueger, Highlands Ranch, CO (US); Li-Mae H. McClellan, Colorado Springs, CO (US); Fiona M. Wohlfarth, Erie, CO (US); Ryan M. Wolsky, Highlands Ranch, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/001,168

(22) Filed: Jun. 6, 2018

(65) Prior Publication Data

US 2018/0280618 A1 Oct. 4, 2018

Related U.S. Application Data

(63) Continuation of application No. 15/135,678, filed on Apr. 22, 2016, now Pat. No. 10,016,560.

(Continued)

(51) Int. Cl.
*A61M 5/172* (2006.01)
*A61M 5/165* (2006.01)
(Continued)

(52) U.S. Cl.
CPC ............ *A61M 5/172* (2013.01); *A61M 5/165* (2013.01); *A61M 5/16804* (2013.01);
(Continued)

(58) Field of Classification Search
CPC .. A61M 2205/3331; A61M 2205/3375; A61M 2205/3379; A61M 39/24;
(Continued)

(56) References Cited

U.S. PATENT DOCUMENTS 3,489,145 A * 1/1970 Judson ................ A61M 1/0209
604/6.02
5,800,383 A 9/1998 Chandler et al.
(Continued)

FOREIGN PATENT DOCUMENTS

WO 2013003570 A1 1/2013
WO 2013044243 A1 3/2013
WO 2014164655 A1 10/2014

*Primary Examiner* — Jason E Flick
(74) *Attorney, Agent, or Firm* — Carter, DeLuca & Farrell LLP

(57) ABSTRACT

A surgical fluid management system includes a source of surgical media, a surgical instrument, a first pump, one or more filters, a second pump, and a controller. The first pump is operatively coupled between the source of surgical media and the surgical instrument. The one or more filters are configured to filter bodily discharge from a surgical site. The second pump is operatively coupled between the one or more filters and the first pump. The controller is in electrical communication with the first pump and the second pump to control the first and second pumps.

18 Claims, 3 Drawing Sheets

Related U.S. Application Data

(60) Provisional application No. 62/151,721, filed on Apr. 23, 2015.

(51) Int. Cl.
  *A61M 5/168* (2006.01)
  *A61M 5/142* (2006.01)
  *A61M 39/24* (2006.01)

(52) U.S. Cl.
  CPC .... *A61M 5/16827* (2013.01); *A61M 5/16854* (2013.01); *A61M 5/16881* (2013.01); *A61M 5/142* (2013.01); *A61M 39/24* (2013.01); *A61M 2205/3331* (2013.01); *A61M 2205/3375* (2013.01); *A61M 2205/3379* (2013.01)

(58) Field of Classification Search
  CPC ...... A61M 5/142; A61M 5/165; A61M 5/172; A61M 13/00; A61M 27/00; A61M 5/16804; A61M 5/16827; A61M 5/16854; A61M 5/16881

USPC .......................................................... 604/67
  See application file for complete search history.

(56) References Cited

U.S. PATENT DOCUMENTS

| | | | |
|---|---|---|---|
| 5,830,180 | A | 11/1998 | Chandler et al. |
| 6,024,720 | A | 2/2000 | Chandler et al. |
| 6,602,221 | B1 | 8/2003 | Saravia et al. |
| 7,204,821 | B1 | 4/2007 | Clare et al. |
| 8,444,592 | B2 | 5/2013 | Williams et al. |
| 9,084,847 | B2 | 7/2015 | Klein et al. |
| 9,233,193 | B2 | 1/2016 | Truckai et al. |
| 9,272,086 | B2 | 3/2016 | Williams et al. |
| 10,016,560 | B2 | 7/2018 | Grim et al. |
| 2007/0078370 | A1 | 4/2007 | Shener et al. |
| 2010/0036313 | A1 | 2/2010 | Shener et al. |
| 2010/0049119 | A1 | 2/2010 | Norman et al. |
| 2016/0361476 | A1* | 12/2016 | Huang .................. C12M 45/02 |

* cited by examiner

FLUID MANAGEMENT SYSTEMS FOR SURGICAL PROCEDURES

CROSS REFERENCE TO RELATED APPLICATIONS

This application is a continuation of U.S. patent application Ser. No. 15/135,678, filed Apr. 22, 2016, which claims the benefit of U.S. Provisional Patent Application No. 62/151,721, filed Apr. 23, 2015, the entire contents of each of which are incorporated by reference herein.

TECHNICAL FIELD

The present disclosure relates to surgical procedures, and more particularly, to surgical systems and methods for managing liquid distending media.

BACKGROUND

Liquid distending media is used in a variety of surgical procedures to swell the organ for adequate visualization of the operative field. Excess absorption of liquid distending media can result in hyponatremia and hypoosmolality. As a result, clinicians closely monitor the amount of fluid absorption during such surgical procedures.

Media absorption volume is currently determined as the difference between the volume of media introduced into a system and the volume of media removed from the system. The accuracy of these measurements is affected by many factors including overfilled media bags, difficulty in measuring intraoperative spillage, and improper media collection.

SUMMARY

Accordingly, the present disclosure is directed to new surgical systems and methods that efficiently and effectively facilitate fluid management for reducing risks associated with the use of liquid distension media. In general, the presently disclosed systems include a source of surgical media (e.g., saline), pumps, sensors, and filters that are operatively coupled to a controller and coordinated to control and monitor a volume of the media introduced into the system and/or absorbed by a patient.

The presently described systems may limit the amount of usable media to an amount suitable for complete patient absorption. Advantageously, the presently described systems provide the benefits of modest dimension, media recycling, and immaculacy appropriate for operating room and clinical settings alike. Other advantages include providing and maintaining user defined pressures within the operating field, filtration sufficient to maintain in vivo visualization, and precise measurement and reporting of media absorption.

In one aspect of the present disclosure, a surgical fluid management system includes a source of surgical media, a surgical instrument, a first pump operatively coupled between the source of surgical media and the surgical instrument, one or more filters configured to filter at least portions of bodily discharge from a surgical site, a second pump operatively coupled between the one or more filters and the first pump, and a controller in electrical communication with the first pump and the second pump to control the first and second pumps.

The surgical fluid management system may further include a pressure sensor in electrical communication with the controller and configured to sense fluid pressure within the surgical instrument.

In some embodiments, the one or more filters may include a first filter supported within a catch basin and a second filter positioned remote from the catch basin. The first filter may be selectively removable from the catch basin and configured to separate tissue from the bodily discharge.

In certain embodiments, the fluid management system may further include one or more fluid conduits extending between the surgical instrument, the catch basin, the one or more filters, the first pump, the second pump, or combinations thereof. The one or more fluid conduits may form a closed loop. At least a first portion of the one or more fluid conduits may be configured to maintain surgical media therein after the controller runs an end surgical cycle to purge at least a second portion of the one or more fluid conduits.

In some embodiments, the surgical fluid management system may further include a check valve operatively coupled to the one or more filters. The check valve may be operatively coupled between the one or more filters and the first pump.

In certain embodiments, one or more of the first and second pumps may be a peristaltic pump.

In some embodiments, the controller may be configured to receive one or more manual inputs. The one or more manual inputs may include pumping pressure, start fill cycle, end fill cycle, start surgical cycle, end surgical cycle, or combinations thereof.

In certain embodiments, the second pump may direct surgical media disposed in the one or more filters toward the source of surgical media when the controller runs an end cycle. The surgical fluid management system may further include a fluid level sensor coupled to the one or more filters and configured to determine a fluid level within the one or more filters.

In some embodiments, the surgical fluid management system may further include a third pump coupled to the one or more filters and in electrical communication with the controller.

In certain embodiments, the surgical fluid management system may further include a fluid level sensor coupled to the source of surgical media and configured to determine an amount of fluid within the source of surgical media.

In some embodiments, the surgical fluid management system may further include one or more ultrasonic sensors in electrical communication with the controller.

According to yet another aspect, a catch basin is provided. The catch basin may include one or more filters configured to separate tissue from bodily discharge, and a lumen for fluid discharge. The one or more filters may be constructed in a conical shape. The lumen may include a valve for regulating fluid flow from the catch basin. The catch basin may further include a fluid level sensor operatively coupled to a controller and configured to determine a fluid level within the catch basin. The controller may work with a pump to control fluid flow from the catch basin.

According to yet another aspect of the present disclosure, a catch basin is provided that may include one or more filters configured to separate tissue from bodily discharge, a lumen for fluid discharge, and a fluid level sensor configured to determine the fluid level within the catch basin.

According to still another aspect of the present disclosure, a method for limiting an amount of surgical media absorbed by a patient during a surgical procedure is provided. The method may include supplying a maximum safe absorbable amount of surgical media from a source of surgical media to a surgical instrument configured to perform a surgical procedure at a surgical site, collecting bodily discharge from the surgical instrument, the surgical site, or combinations thereof; directing at least portions of collected bodily discharge into one or more filters, filtering surgical media from the collected bodily discharge with the one or more filters, directing filtered surgical media from the one or more filters to the surgical instrument, and selectively supplying surgical media from the source of surgical media to the surgical instrument.

The method may further include autonomously controlling a volume of surgical media supplied from the source of surgical media.

The method may further include maintaining a predetermined fluid pressure through the surgical instrument based upon a manual input received by a controller operatively coupled to the source of surgical media via one or more pumps.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein.

DETAILED DESCRIPTION

Figure 1:
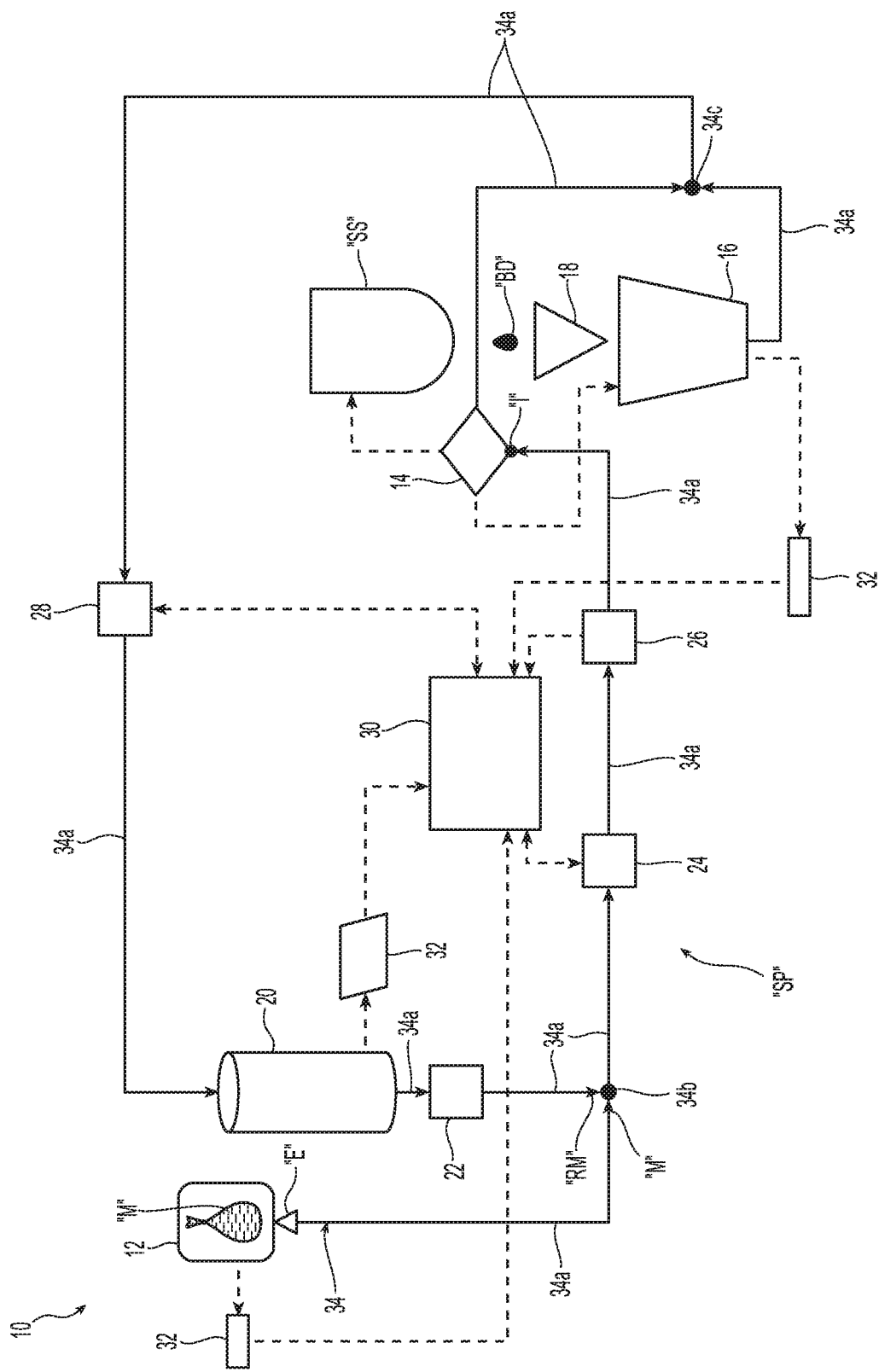
FIG. 1 is a schematic illustration of one embodiment of a surgical fluid management system in accordance with the present disclosure.

Particular embodiments of the present disclosure are described hereinbelow with reference to the accompanying drawings in which like reference numerals designate identical or corresponding elements in each of the several views. In the following description, well-known functions or constructions are not described in detail to avoid obscuring the present disclosure in unnecessary detail.

In accordance with the present disclosure, surgical fluid management systems and/or components thereof (e.g., surgical instruments) can be used in any suitable surgical procedure involving liquid distention media (e.g., transurethral resection of the prostatectomy commonly known as TURP). Obviously, different components, connections, and considerations apply to each particular type of procedure; however, the aspects and features of the present disclosure remain generally consistent regardless of the particular procedure and/or components used.

In the interest of brevity, although surgical fluid management systems of the present disclosure can be used in connection with any suitable surgical procedure as described above, the presently disclosed surgical fluid management systems will only be described herein in connection with intrauterine surgical procedures such as myomectomy, the surgical removal of fibroids from a patient's uterus.

Turning now to FIG. 1, a surgical fluid management system in accordance with the present disclosure is generally referred to as 10. The surgical fluid management system 10 includes a source of surgical media 12 that supports surgical media "M" therein. For instance, the source of surgical media 12 may include a predetermined volume of saline (e.g., two or three liters), which may be a critical absorption volume and/or a volume that can be safely fully absorbed by a patient. The surgical fluid management system 10 further includes a surgical instrument 14 configured to perform a surgical procedure at a surgical site "SS." For instance, during a myomectomy procedure, the surgical instrument 14 can include a resectoscope, which includes one or more inlet and/or outlet passages (not shown) for liquid distension media at surgical site "SS" such as a patient's uterus. The surgical instrument 14 may also be coupled to an electrosurgical energy source (e.g., a generator—not shown) to enable an end effector (not shown) of the surgical instrument 14 to perform a function such as tissue resection via radiofrequency energy or the like.

A catch basin 16 is positioned to receive bodily discharge "BD" from the surgical instrument 14 and/or the surgical site "SS." The bodily discharge "BD" includes blood, tissue and/or other solid matter/particulate, and/or surgical media "M." The catch basin 16 supports one or more tissue filters 18 that function to filter tissue and/or other solid matter/particulate from the bodily discharge "BD" while enabling blood and/or surgical media "M" to pass therethrough into catch basin 16. The tissue filter 18 may be configured to be supported at least partially within the catch basin 16, for example, at least half way into the catch basin 16 to limit risks of overflow and/or spillage. A portion of the tissue filter 18 may project from the catch basin 16. In some embodiments, the tissue filter 18 may include mesh. In certain embodiments, the mesh of the tissue filter 18 may be any suitable fine grade such as 1/16 inch. In some embodiments the tissue filter 18 may have a conical configuration or the like that is configured to minimize the forming of particles and slivers while minimizing back splash. In certain embodiments, the tissue filter 18 may be formed of any suitable material such as aluminum.

A second filter 20, which may be positioned remote from the catch basin 16, functions to filter red and/or white blood cells from the bodily discharge "BD" to separate the surgical media "M" therefrom and to achieve translucency and/or transparency for improved visualization during reuse/recycling back through surgical instrument 14 (e.g., as a distention fluid at the surgical site "SS") as described in greater detail below. In certain embodiments, second filter 20 includes a capsule depth filter. In some embodiments, the second filter 20 may include a capsule depth filter with double-skinned hollow fibers and a polyethersulfone membrane having an average pore size of approximately 0.02 micrometers. A check valve 22 is operatively coupled to the second filter 20 and functions to prevent air bubbles from entering the surgical system 10.

A first pump 24 is operatively coupled between the source of surgical media 12 and the surgical instrument 14. The first pump 24 is configured to draw surgical media "M" from the source of surgical media 12, the second filter 20, or combinations thereof. The first pump 24 is also configured to direct the surgical media "M" to the surgical instrument 14 and through a feedback sensor such as a pressure sensor 26 configured to sense fluid pressure within the surgical instrument 14 and/or at an inlet "I" thereof. The pressure sensor 26 may be in electrical communication with a controller 30 (e.g., a labview interface) as a described in greater detail below.

A second pump 28 is operatively coupled between the catch basin 16 and the second filter 20 to draw at least portions of the bodily discharge "BD" from the catch basin 16 (e.g., fluid portions including blood and/or surgical media "M") and direct the fluid portions (or substantially fluid portions) of the bodily discharge "BD" to the second filter 20. One or both of the first and second pumps 24, 28 may be peristaltic pumps. The first and/or second pumps 24, 28 may be configured to pump uni-directionally, such as in a downstream direction, and/or bi-directionally, such as in upstream and/or downstream directions.

The controller 30 is in electrical communication with the first pump 24 and the second pump 28 to selectively control activation of the first and/or second pumps 24, 28. For instance, the controller 30 can be configured to selectively turn the first and/or second pumps 24, 28 on and/or off. The controller 24 may also be in electrical communication with one or more feedback sensors such as fluid level sensors 32 that couple to one or more of the catch basin 16, the second filter 20, and/or the source of surgical media 12 to determine and/or control respective fluid levels therein. In some embodiments, the pressure sensor 26 and/or the fluid level sensors 32 may include an ultrasonic sensor.

The controller 30 may be configured to receive one or more manual inputs such as pumping pressure (e.g., between about 60-100 mmHg), start fill cycle, end fill cycle, start surgical cycle, and/or end surgical cycle to run, stop, and/or automate the surgical fluid management system 10 as described in greater detail below.

A fluid conduit assembly 34 includes one or more fluid conduits 34a and first and second conduit connectors 34b, 34c (e.g., T-connectors or the like). The fluid conduit assembly 34 extends between and couples one or more components of the surgical fluid management system 10 including the source of surgical media 12, the surgical instrument 14, the catch basin 16, the second filter 20, check valve 22, the first pump 24, the pressure sensor 26, and/or the second pump 28. The fluid conduit assembly 34 or portions thereof may form a closed loop.

In use, the controller 30 initiates a fill cycle in which the first pump 24 draws an initial volume of surgical media "M" through the fluid conduit assembly 34 to the surgical instrument 14. The surgical media "M" is dispensed through the surgical instrument 14 to the surgical site SS and into the catch basin 16 to fill the catch basin 16 to a threshold volume which may be determined by a fluid level sensor 32 coupled to the catch basin 16. Once a threshold volume is established, the second pump 28 may be activated to draw fluid, namely the surgical media "M," from the catch basin 16 in order to fully pressurize the system 10.

After the system 10 is fully pressurized with all air removed from the system 10, the controller 28 can receive an input such as a predetermined pressure value (e.g., a mean arterial pressure of the patient). The predetermined pressure value may be manually and/or robotically input to the controller 28. The controller 28 can then initiate a surgical start cycle, which can also be manually and/or robotically initiated, such that the system 10 maintains fluid pressure throughout at least portions of the system 10 at the predetermined pressure value received by the controller 28. A surgical procedure, such as myomectomy, can then be performed at the surgical site "SS" with the surgical instrument 14.

During the surgical procedure, bodily discharge "BD" is filtered through tissue filter 18 such that fluids of the bodily discharge "BD" are received in the catch basin 16 with solid and/or particulate matter such as tissue filtered by first filter 18. Fluids, which can include, for example, blood and/or surgical media "M" as described above, are pumped through the surgical instrument 14 and/or out of the catch basin 16, so that these fluids merge downstream at the second conduit connector 34c and are pumped by the second pump 28 to the second filter 20. The second filter 20 filters out the red and/or white blood cells from these fluids to separate the surgical media "M" therefrom. Once filtered through the second filter, the surgical media "M" is then recycled/reintroduced into the first conduit connector 34b through the check valve 22.

As indicated by arrow "RM," the first pump 24 then pumps the recycled surgical media "M" and any additional surgical media "M" needed from the source of surgical media 12 to maintain the fluid pressure in the system 10, toward the surgical instrument 14. The pressure sensor 26 and/or any fluid level sensors 32 communicate with the controller 30 to maintain the desired fluid pressure in the system 10 via selective communication with and/or activation of first and second pumps 24, 28. This process is continuously repeated/looped until the surgical procedure is complete and/or until the volume of surgical media "M" of the source of surgical media 12 is reduced to a minimum threshold and/or critical volume. The minimum threshold/critical volume can be a maximum volume absorbable by the patient to prevent liquid distension media absorption complications such as hypervolemia and/or hyponatremia.

Advantageously, recycling of such surgical media "M" lowers the volume of total surgical media used as new and/or additional surgical media does not continuously need to be drawn from the source of surgical media 12. Further, since blood and/or white cells are filtered out of the recycled surgical media, visualization at the surgical site "SS" can be continuously maintained throughout the surgical procedure.

An end surgical cycle/purge can then be initiated through controller 30 to purge the system 10. When the end surgical cycle is initiated, the controller 30 communicates with the second pump 28 to pump recycled surgical media "RM" (e.g., from catch basin 16, surgical instrument 14, and/or second filter 20) back toward the source of surgical media 12 as indicated by arrow "E." A difference between an initial volume of surgical media "M" in the source of surgical media 12 before the fill cycle is initiated and a final volume of surgical media "M" in the source of surgical media 12 after end surgical cycle is complete, can be calculated to establish an approximate volume of surgical media "M" absorbed by the patient. As a factor of safety, some surgical media "M" may remain in a safety portion "SP" of the system 10 between conduit connector 34b and an inlet end "I" of surgical instrument 14. A closer approximation of absorbed surgical media "M" can be established based upon a volume capacity of the safety portion "SP," which can be added to the final volume of surgical media "M" in the source of surgical media 12.

Additionally, and/or alternatively, one or more pumps, sensors, fluid sources (e.g., gas, air, etc.) (not shown) and/or additional fluid conduits 34a and/or connectors 34b can be coupled to the system 10 (e.g., between the safety portion "SP" and/or the source of surgical media 12) and arranged to enable the surgical media "M" disposed in the safety portion "SP" to be pumped and/or directed into the source of the surgical media 12 in an upstream and/or downstream direction. In some embodiments, the first pump 24 may be configured for bi-directional pumping to enable fluid in the safety portion "SP" to be pumped to the source of surgical media 12.

Advantageously, the presently described surgical fluid management systems can provide highly accurate and/or precise estimations of media absorption volumes.

The first filter 18 can be selectively removed from the catch basin 16 so that any solid matter and/or tissue filtered/captured by the first filter 18 can be later analyzed and/or tested.

Figure 2:
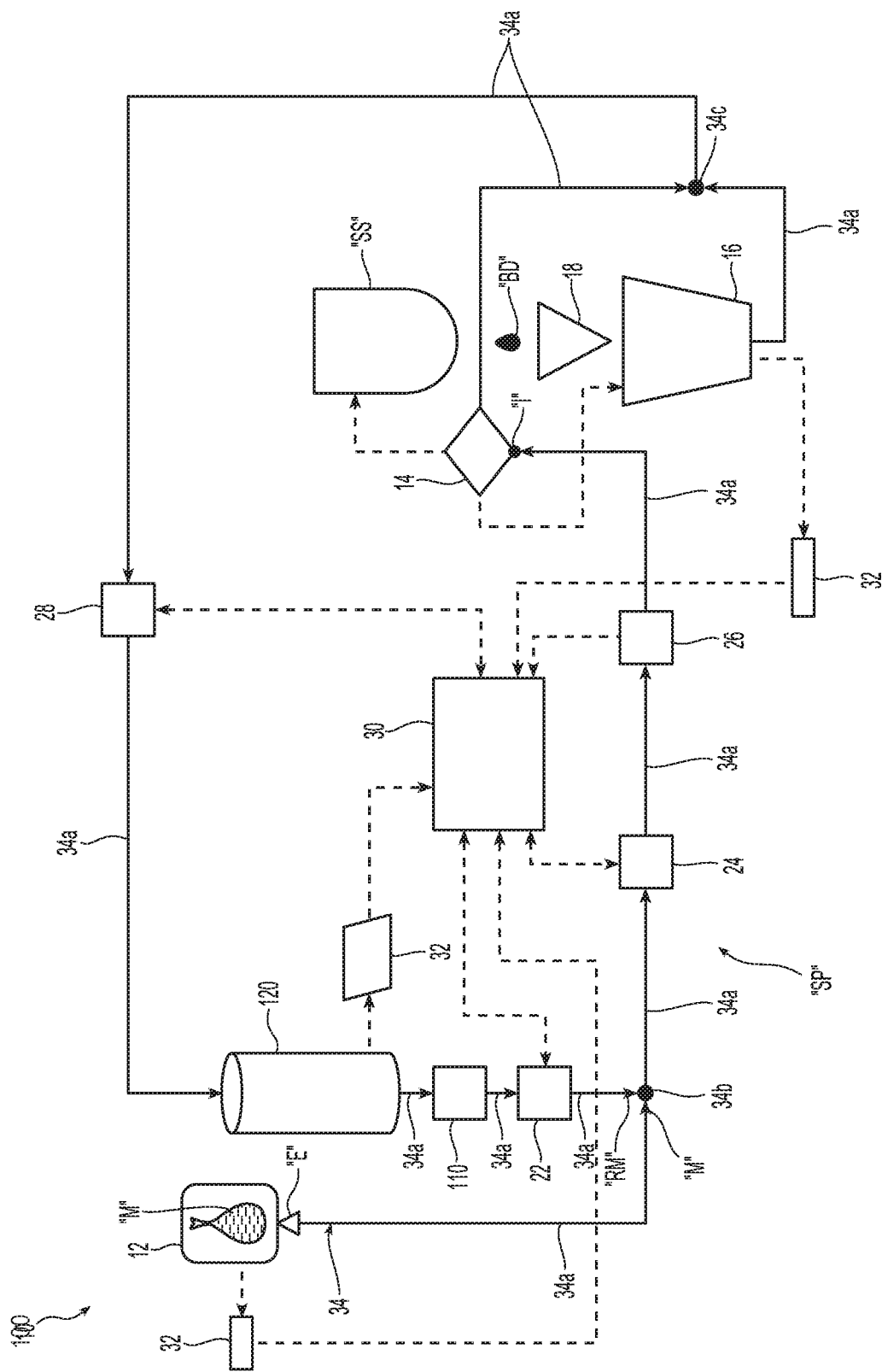
FIG. 2 is a schematic illustration of another embodiment of a surgical fluid management system in accordance with the present disclosure.

As seen in FIG. 2, another embodiment of a surgical fluid management system, generally referred to as surgical fluid management system 100, is provided. Surgical fluid management system 100 is substantially similar to surgical fluid management system 10 except the surgical fluid management system 100 includes another embodiment of a second filter 120 and a third pump 110 connected between the check valve 22 and the second filter 120 to facilitate extraction/removal of surgical media "M" from the second filter 120.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely control the instruments via the robotic surgical system. As can be appreciated, a highly skilled clinician may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the clinician to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the clinician. The scale factor or gearing ratio may be adjustable so that the operator can control the resolution of the working ends of the surgical instrument(s).

The master handles may include various sensors to provide feedback to the clinician relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the clinician with enhanced tactile feedback simulating actual operating conditions. The master handles may also include a variety of different actuators for delicate tissue manipulation or treatment further enhancing the clinician's ability to mimic actual operating conditions.

Figure 3:
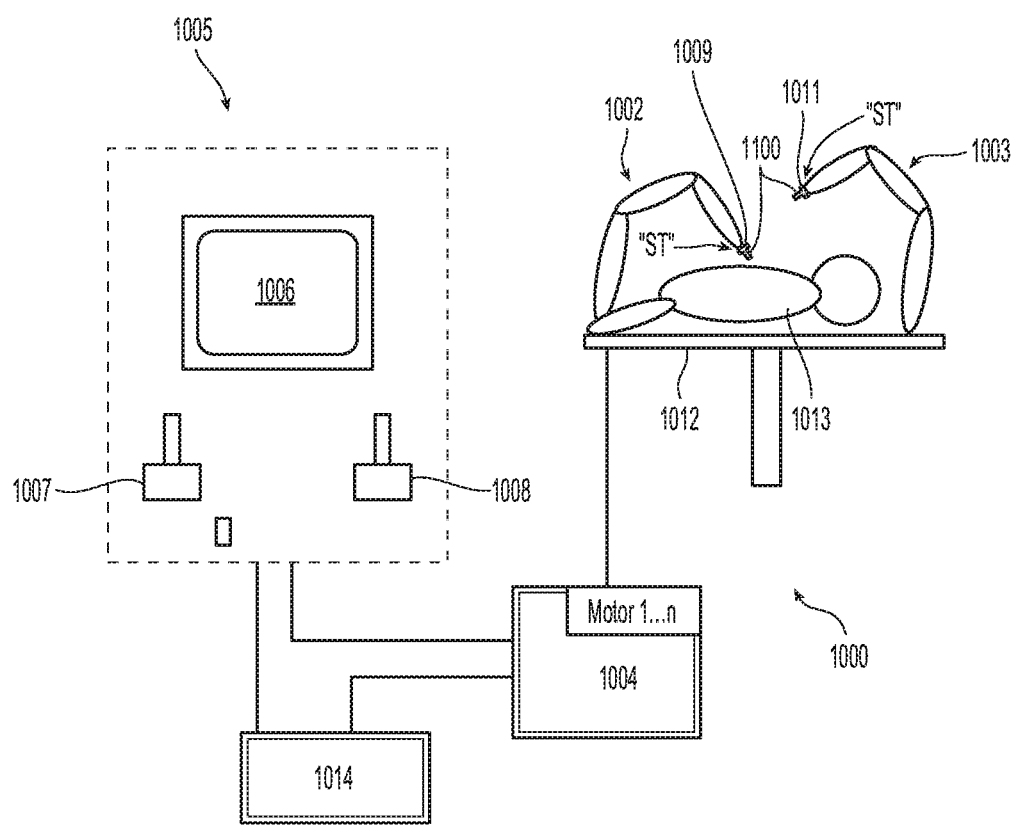
FIG. 3 is a schematic illustration of a medical work station and operating console in accordance with the present disclosure.

Referring also to FIG. 3, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a clinician, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical instrument or surgical tool "ST" (e.g., a resectoscope) supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient "P" lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being "P" and/or anatomical atlases.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:
1. A surgical fluid management system, comprising:
a source of surgical media;
a surgical instrument;
a first pump operatively coupled between the source of surgical media and the surgical instrument;
a first filter configured to filter at least portions of bodily discharge from a surgical site;
a second pump operatively coupled between the first filter and the first pump; and a controller in electrical communication with the first pump and the second pump to control the first and second pumps; and a fluid conduit extending between the surgical instrument and the source of surgical media, wherein the fluid conduit forms a closed loop configured to return at least a portion of a surgical media from the surgical instrument to the source of surgical media.

2. The surgical fluid management system of claim 1, further including a pressure sensor in electrical communication with the controller and configured to sense fluid pressure within the surgical instrument.

3. The surgical fluid management system of claim 1, further comprising a catch basin and a second filter, wherein the first filter is supported within the catch basin and selectively removable from the catch basin, and the second filter is positioned remote from the catch basin.

4. The surgical fluid management system of claim 1, wherein at least a first portion of the fluid conduit is configured to maintain the surgical media therein after the controller runs an end surgical cycle to purge at least a second portion of the fluid conduit.

5. The surgical fluid management system of claim 1, further including a check valve operatively coupled to the first filter.

6. The surgical fluid management system of claim 5, wherein the check valve is operatively coupled between the first filter and the first pump.

7. The surgical fluid management system of claim 1, wherein at least one of the first or second pumps is a peristaltic pump.

8. The surgical fluid management system of claim 1, wherein the controller is configured to receive a manual input.

9. The surgical fluid management system of claim 8, wherein the manual input includes pumping pressure, start fill cycle, end fill cycle, start surgical cycle, end surgical cycle, or combinations thereof.

10. The surgical fluid management system of claim 1, wherein when the surgical media is disposed in the first filter, the second pump directs the surgical media toward the source of surgical media in response to the controller running an end cycle.

11. The surgical fluid management system of claim 10, further including a fluid level sensor coupled to the first filter.

12. The surgical fluid management system of claim 1, further including a third pump coupled to the first filter and in electrical communication with the controller.

13. The surgical fluid management system of claim 1, further including a fluid level sensor coupled to the source of surgical media.

14. The surgical fluid management system of claim 1, further including an ultrasonic sensor in electrical communication with the controller.

15. A surgical fluid management system, comprising:
a source of surgical media;
a surgical instrument;
a first pump operatively coupled between the source of surgical media and the surgical instrument;
a first filter configured to filter at least portions of bodily discharge from a surgical site;
a second pump operatively coupled between the first filter and the first pump;
a controller in electrical communication with the first pump and the second pump to control the first and second pumps; and
a fluid conduit extending between the surgical instrument and at least one of:
the first filter, the first pump, the second pump, or combinations thereof,
wherein at least a first portion of the fluid conduit is configured to maintain surgical media therein after the controller runs an end surgical cycle to purge at least a second portion of the fluid conduit.

16. The surgical fluid management system of claim 15, further comprising a catch basin and a second filter, wherein the first filter is supported within the catch basin and selectively removable from the catch basin, and the second filter is positioned remote from the catch basin.

17. The surgical fluid management system of claim 15, wherein the controller is configured to receive a manual input including pumping pressure, start fill cycle, end fill cycle, start surgical cycle, end surgical cycle, or combinations thereof.

18. A surgical fluid management system, comprising:
a source of surgical media;
a surgical instrument;
a fluid conduit extending between the surgical instrument and the source of surgical media, wherein the fluid conduit forms a closed loop configured to return at least a portion of a surgical media from the surgical instrument to the source of surgical media;
a catch basin defining a lumen, the catch basin configured to receive a bodily discharge including the portion of the surgical media;
a filter supported by the catch basin and configured to separate tissue from the bodily discharge;
a valve supported by the lumen and configured to regulate fluid flow from the catch basin;
a fluid level sensor configured to emit a signal based upon a fluid level within the catch basin;
a controller in communication with the fluid level sensor; and
a pump operatively coupled to the controller.

* * * * *